(12) United States Patent
Wu et al.

(10) Patent No.: US 10,332,255 B2
(45) Date of Patent: Jun. 25, 2019

(54) METHOD FOR ASSESSING STENOSIS SEVERITY IN A LESION TREE THROUGH STENOSIS MAPPING

(71) Applicants: Zhongle Wu, Troy, MI (US); Jorey Chernett, Bloomfield Hills, MI (US)

(72) Inventors: Zhongle Wu, Troy, MI (US); Jorey Chernett, Bloomfield Hills, MI (US)

( * ) Notice: Subject to any disclaimer, the term of this patent is extended or adjusted under 35 U.S.C. 154(b) by 601 days.

(21) Appl. No.: 14/965,118

(22) Filed: Dec. 10, 2015

(65) Prior Publication Data

US 2016/0098531 A1  Apr. 7, 2016

Related U.S. Application Data

(63) Continuation-in-part of application No. 14/643,024, filed on Mar. 10, 2015, now abandoned, and a
(Continued)

(51) Int. Cl.
| | | |
|---|---|---|
| *A61B 5/00* | (2006.01) | |
| *G06T 7/00* | (2017.01) | |
| *A61B 6/00* | (2006.01) | |
| *A61B 8/08* | (2006.01) | |
| *A61B 5/02* | (2006.01) | |
| *A61B 5/021* | (2006.01) | |

(Continued)

(52) U.S. Cl.
CPC ............ *G06T 7/0014* (2013.01); *A61B 5/021* (2013.01); *A61B 5/02007* (2013.01); *A61B 5/02035* (2013.01); *A61B 5/0263* (2013.01); *A61B 5/1075* (2013.01); *A61B 5/7282* (2013.01); *A61B 6/504* (2013.01); *A61B 8/0891* (2013.01); *G06F 19/00* (2013.01); *G16H 50/50* (2018.01); *A61B 5/0044* (2013.01); *A61B 5/7278* (2013.01); *A61B 2576/00* (2013.01); *A61B 2576/023* (2013.01); *G06T 2207/10101* (2013.01); *G06T 2207/10132* (2013.01); *G06T 2207/30048* (2013.01); *G06T 2207/30104* (2013.01)

(58) Field of Classification Search
CPC ... G06F 19/3437; G06F 19/00; G06T 7/0014; G06T 2207/30048; G06T 2207/10132; G16H 50/50; A61B 5/1075; A61B 5/02035; A61B 5/0263; A61B 5/02007; A61B 5/7282; A61B 5/021; A61B 6/504; A61B 8/0891

See application file for complete search history.

(56) References Cited

U.S. PATENT DOCUMENTS

| | | | | |
|---|---|---|---|---|
| 8,249,815 | B2 * | 8/2012 | Taylor | ............... A61B 5/02007 |
| | | | | 702/19 |
| 8,977,339 | B1 * | 3/2015 | Wu | .................... A61B 5/02007 |
| | | | | 600/407 |

* cited by examiner

*Primary Examiner* — Joel Lamprecht
(74) *Attorney, Agent, or Firm* — John S. Artz; Dickinson Wright PLLC

(57) ABSTRACT

A method of assessing stenosis severity for a patient includes generating a three dimensional model of a lesion specific vessel tree of the patient. A plurality of inlet and outlet positions are identified in the lesion tree. A total flow rate from the vessel tree model is estimated. A processor and task specific software are utilized to perform computational fluid dynamic simulation on the vessel tree. A flow rate and apparent flow resistance for each of the outlets is then determined. At least one ideal model is generated. A computational fluid dynamic simulation is performed on the at least one ideal model. A level of stenosis severity is determined for each of the outlets.

22 Claims, 9 Drawing Sheets

Related U.S. Application Data continuation of application No. 14/172,594, filed on Feb. 4, 2014, now Pat. No. 8,831,315.

(60) Provisional application No. 62/205,466, filed on Aug. 14, 2015.

(51) Int. Cl.
*A61B 5/026* (2006.01)
*A61B 5/107* (2006.01)
*G16H 50/50* (2018.01)
*G06F 19/00* (2018.01)

METHOD FOR ASSESSING STENOSIS SEVERITY IN A LESION TREE THROUGH STENOSIS MAPPING

CROSS-REFERENCE TO RELATED APPLICATIONS

The present application claims priority to U.S. Provisional Patent Application Ser. No. 62/205,466, filed Aug. 14, 2015 and entitled "System and Method for Assessing Stenosis Severity Through Stenosis Mapping" and is also a continuation-in-part of U.S. patent application Ser. No. 14/643,024, filed Mar. 10, 2015 and entitled "Method for Assessing Stenosis Severity Through Stenosis Mapping", which is a continuation of U.S. Pat. No. 8,831,315, filed Dec. 5, 2013 and entitled "Method for Assessing Stenosis Severity Through Stenosis Mapping", the disclosures of which are all hereby incorporated by reference as though set forth fully herein.

TECHNICAL FIELD

The present disclosure broadly relates to a method of accurately identifying and diagnosing coronary artery disease. More specifically, the present disclosure relates to a noninvasive method of accurately identifying and diagnosing coronary artery disease as it relates to lesions of complex morphologies in a vessel tree through stenosis severity mapping.

BACKGROUND OF THE INVENTION

Coronary artery disease (CAD) is a common type of heart disease and leading cause of death in the United States in both men and women. CAD is often caused when the arteries that supply blood to the heart muscle become hardened and narrowed and thus permit less blood to flow therethrough. When this occurs, the heart muscle cannot get the required blood and oxygen it needs, which can lead to chest pain or a heart attack. According to statistics, each year CAD affects some 16 million people in the U.S., causes approximately 1.2 million heart attacks, and is responsible for over 450,000 deaths.

Early detection techniques and procedures have been developed in order to diagnose CAD and determine whether treatment is necessary. However, current diagnostic techniques are often equivocal, which results in a significant number of low to mid risk patients being unnecessarily admitted from emergency rooms to the hospital for further testing. After further testing, CAD is ruled out for many of these low to mid risk patients, which results in unnecessary costs exceeding $10 billon.

Invasive diagnostic techniques for CAD are known, but they are extremely expensive. One common invasive imaging technique is coronary catheter/angiography (CA). With CA, a catheter is inserted into a person's artery and a contrast agent or dye is injected therein. As the contrasted blood flows through the artery, any narrowing areas of a vessel can be readily seen, which can indicate the presence of plaque. Another known invasive imaging technique is intravascular ultrasound (IVUS), which involves the insertion of an IVUS catheter into a blood vessel. The catheter includes a transducer that emits a beam within the artery to gauge the location of the surrounding vessel. The resulting vessel shape that is determined can reveal the presence of any plaque. Another known invasive technique is optical coherence tomography (OCT), which is an interferometric technique that typically employs near-infrared light to capture three-dimensional images from within the artery to show the existence of any plaque.

Due to the cost and invasive nature of these techniques, non-invasive diagnostic techniques have been developed to assist in determining the existence of CAD. While these non-invasive techniques are less expensive, they have limitations. One such increasingly employed technology is coronary computed tomography angiography (CCTA), which non-invasively obtains anatomic data of the vessel and surrounding structures for evaluation of the severity of artery stenosis. In general, CCTA gathers this data through high resolution cardiac imaging. The resultant imaging allows for the assessment of any luminal narrowing and/or atherosclerotic plaque that can cause the stenosis.

Armed with the CCTA data, there are various methods of assessing a coronary artery lumen for stenosis, including visual assessment and quantitative assessment of the stenosis. These methods can be performed manually, semi-automatically or fully automatically using the CCTA data. Commonly used assessment methods include estimating the narrowed diameter of an artery (luminal diameter stenosis) or the narrowed artery area (luminal area stenosis) to grade the severity of stenosis. Such estimates generally involve defining clinically relevant coronary stenosis based on a predetermined percentage of luminal diameter stenosis or luminal area stenosis, i.e., 50%. Generally, the diagnostic performance of these methods provides good sensitivity and specificity for detecting significant severe stenosis.

However, in cases where intermediate stenosis lesions exist, the specificity and accuracy of this method is lower, despite its high negative prediction value. One known cause for this low specificity is that the luminal diameter stenosis and luminal area stenosis assessment techniques may lead cardiac surgeons to overestimate CAD severity similar to rates reported by cardiologists and radiologists. The overestimation of stenosis severity with CCTA may be affected by the assessment of the luminal diameter within the cross-section image since coronary arteries enlarge in response to athermanous plaque growth, a phenomenon referred to as "remodeling". The overestimation/underestimation and low specificity of stenosis severity may also be affected by the not uncommon existence of irregular arterial lumen shapes at lesion sites. As such, the luminal diameter assessment technique may misrepresent true lumen narrowing in many instances, which does not solve the issue of unnecessary costs associated with accurately assessing the existence of CAD.

The difficulty with these types of assessment techniques can be illustrated by the schematic diagram of FIG. 1, which depicts four examples (A) through (D) of different stenosis severity each having lesions of different geometries. Each of these examples illustrates a condition with a geometric luminal diameter stenosis of 50%. In other words, each of the examples illustrates an effective reduction in the vessel diameter to 50% at the narrowest point with each example including lesions of different shapes, locations and/or sizes. FIG. 2 exemplarily illustrates how these different examples of 50% luminal diameter stenosis can have different stenosis severities. As shown, examples (A) through (D) of FIG. 1 are each mapped to an illustration of standard regular shaped stenosis, which are assumed to have the same blood flow pressure drop from before the stenosis to after the stenosis. As shown, the examples in the bottom of FIG. 2 have different stenosis severities despite each having the same geometric luminal diameter stenosis. This mapping thus illustrates the inaccuracy that can result when evaluating intermediate stenosis regions that have irregular shapes based on luminal diameter and luminal area techniques.

With recent advancements in blood flow hemodynamics, computational fluid dynamics (CFD) simulations have been successfully utilized to predict blood flow characteristics in arteries such as spatial and temporal variations of flow rate and pressure to assist in diagnosing CAD. FFRct and virtual FFR are two recent examples where CFD has been used to predict fractional flow reserve (FFR), which is defined as the pressure distal to a stenosis relative to the pressure before the stenosis. A significant change in this relative pressure will tend to indicate the presence of CAD, i.e., reduced flow rate. FFR has been recognized as the gold standard for intermediate lesion assessment by the European Society of Cardiology. FFR measurement, however, is an invasive method where a pressure sensitive angioplasty wire is placed directly into the coronary artery through coronary catheterization. The FFRct method is complicated as it uses computational modeling on the CCTA for the whole coronary artery tree including a segment of the aorta artery. The virtual FFR method is similarly complicated as it uses computation modeling on the rotational coronary angiography (RoCA) images for the whole major vessel.

Both the FFRct and virtual FFR methods attempt to simulate blood flow in physiologically realistic terms. This requires the estimation of sophisticated boundary conditions and initial conditions, which can be difficult to estimate accurately. In addition, computational modeling requires significant resources (both computational and labor) to segment the whole coronary artery tree domain or the whole vessel domain to construct the patient specific arterial lumen geometry as input to the CFD. This also requires a large domain of patient specific arterial models in order to perform simulations close to the physiological environment to accurately predict FFR. The requirement of a large domain has various disadvantages. One disadvantage is that CFD simulation needs large computational resources as it is a computational insensitive algorithm. Another disadvantage is that the large domain requirement limits the number of CCTA scans that may be used due to the localized low image quality on a normal vessel. Additionally, imaging artifacts such as blurring of motion under limited temporal resolution of imaging, blooming artifacts from calcified plaques under limited spatial resolution of imaging, or even localized noise are more likely to appear in a large domain. This, in turn, reduces the confidence level of the prediction of CAD by the CFD simulation for FFR value.

Due to the limitations with the above treatment methods, the Applicant developed a new technique for assessing stenosis severity. This technique which is the subject of U.S. Pat. No. 8,831,315 is a non-invasive process that involves generating a three dimensional model of one or more lesions of interest based on anatomical imaging of a patient. The model that is constructed of the vessel with lesions is limited to a vessel with a single inlet and one or more outlets. The technique also involves creating a series of comparative two dimensional lesion specific models having conditions that correspond to the generated three dimensional model. Each of the comparative two dimensional models represents a vessel having one or more regular shaped lesions within the vessel, which lesions are differently configured so that each two dimensional vessel model represents a different known level of stenosis severity. The three dimensional model, which is based on user anatomical data, is then mapped to the appropriate two dimensional model to determine a quantitative measure of stenosis severity of the patient's CAD. This technique has been highly useful for simple stenosis morphology in a vessel with only a single segment. This technique, however, has limitations for more complex morphologies of lesions as the accuracy may be affected by the selected flow path despite the fact that the technique has compensated for area difference between the inlet to outlet by using the inlet and outlet radii.

SUMMARY OF THE INVENTION

It is therefore an aspect of the disclosure to provide a non-invasive method for accurately assessing complex luminal diameter stenosis in a vessel lesion tree.

It is another aspect of the disclosure to provide a method for assessing stenosis severity across multiple vessels in a lesion tree that is less expensive than prior methods.

It is a further aspect of the disclosure to provide a method for assessing stenosis severity across multiple vessels of a lesion tree that provides more meaningful assistance in clinically diagnosing CAD.

It is still another aspect of the disclosure to provide a method for assessing stenosis severity across multiple vessels that can evaluate complex morphologies of lesions.

It is still a related aspect of the disclosure to provide a method for assessing stenosis severity that can evaluate lesions across bifurcation of vessels.

It is yet another related aspect of the disclosure to provide a method for assessing stenosis severity that can evaluate lesions distributed across multiple vessels.

In accordance with the above and the other aspects, a method of assessing stenosis severity for complex morphologies of lesions in a lesion tree is provided. According to the method, a processor and task specific software are employed to generate a three dimensional model of a lesion specific vessel tree of the patient. Positions for an inlet and a plurality of outlets can then be determined. A total flow rate for the vessel tree model can then be estimated. The processor and task specific software can then be utilized to perform computational fluid dynamic simulation on the vessel tree. The flow rate and apparent flow resistance can be determined for each of the outlets of the vessel tree. A plurality of ideal models representing different narrowing levels of stenosis severity each with ideal shaped stenosis can be generated utilizing the processor and the task specific software. Computational fluid dynamics can be performed on the plurality of ideal modes to map the three dimensional model to an equivalent generated model. The level of stenosis severity can then be determined at each of the outlets.

BRIEF DESCRIPTION OF THE DRAWINGS

Other aspects of the present disclosure will be readily appreciated, as the same becomes better understood by reference to the following detailed description when considered in connection with the accompanying drawings wherein.

DETAILED DESCRIPTION OF THE INVENTION

Figure 1:
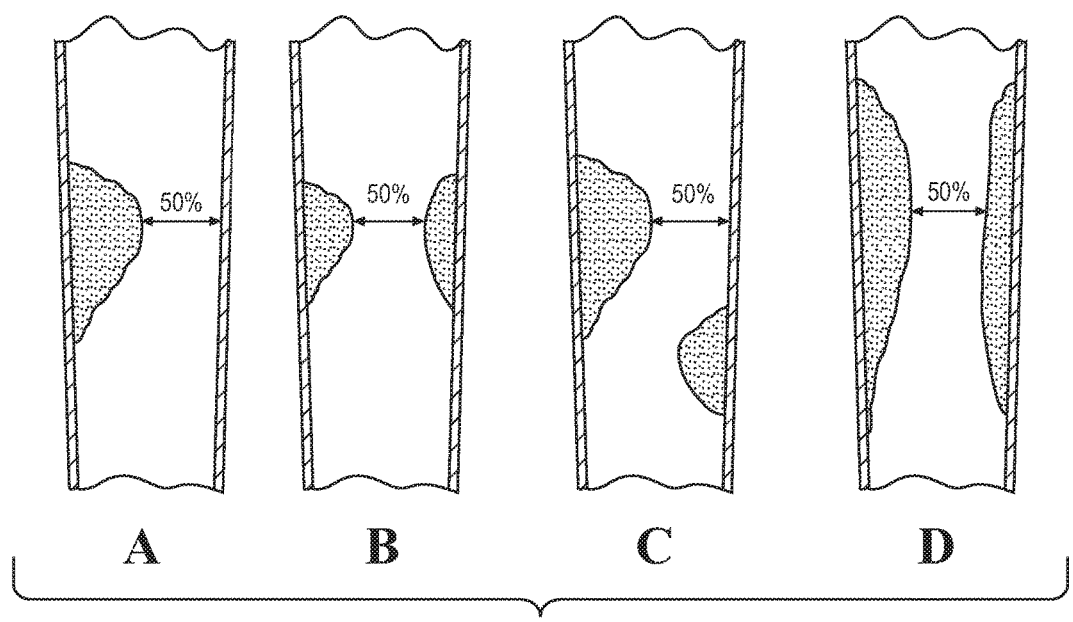
FIG. 1 is a schematic illustration of various examples of stenosis severity having different irregular shaped stenosis and a resulting luminal diameter of 50%.
Figure 2:
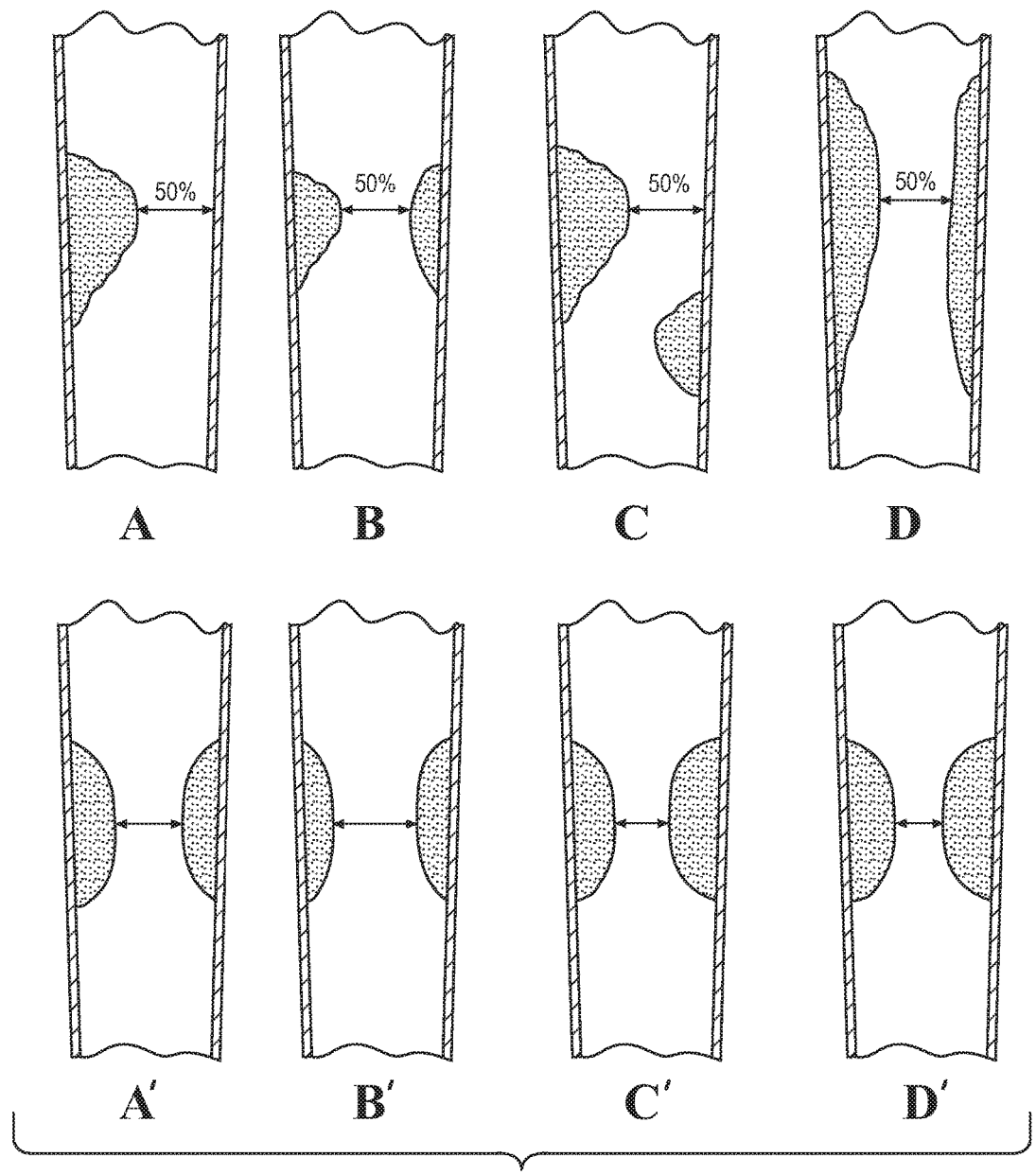
FIG. 2 is a schematic illustration of how each of the irregular-shaped stenosis examples of FIG. 1 correspond to regular shaped stenosis illustrations.
Figure 3:
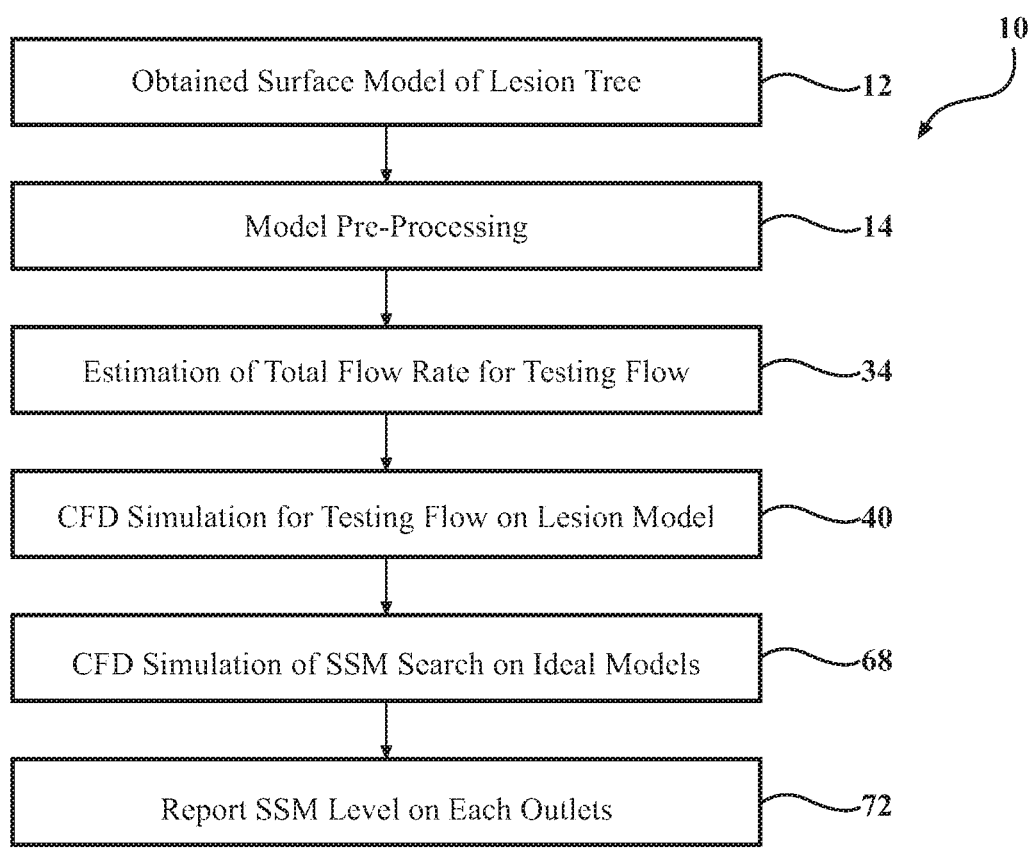
FIG. 3 illustrates a block diagram of a method of determining stenosis severity in a human blood vessel in the accordance with an aspect of the disclosure.

The present disclosure relates to a method of determining the stenosis severity of an artery, such as a coronary artery, and particularly as it relates to irregular-shaped stenosis or complex morphology of lesions. It will be appreciated, however, that the present disclosure applies to any type of shaped stenosis or any sized stenosis. FIG. 3 schematically illustrates a method 10 in accordance with an aspect of the present disclosure that provides accurate stenosis mapping for complex stenosis in a lesion vessel tree using a computational fluid dynamic ("CFD") based method in which all outlet branches can be evaluated using a single testing flow with stenosis severity being applied to each outlet branch.

According to an aspect, relevant data about a patient to be evaluated is initially obtained. The relevant patient data may include patient anatomical data and particularly imaging data of the pertinent areas of concern. The patient anatomical data may be obtained by using a noninvasive imaging method such as CCTA. According to CCTA, a computed tomography (CT) machine may be used to scan images of structures, such as the heart region for diagnosis of the coronary artery vessels. The scanned data that results from this imaging method generally includes a stack of images that may then be assembled into a three-dimensional image, which may then be utilized for further diagnostics. Alternatively, other noninvasive three dimensional imaging methods such as magnetic resonance imaging (MRI) or ultrasound (US) may be used. Alternatively, invasive imaging methods, such as digital subtraction angiography (DSA) or rotational coronary angiography (RoCA) may also be used to image the structures of the patient's anatomy for further use. Other suitable imaging methods may also be utilized.

According to an aspect, the relevant patient data that is initially obtained may also include other patient information that may assist with the assessment of stenosis severity. Such patient data may include a patient's blood pressure, heart rate, weight, hematocrit, or a variety of other patient information that may be relevant to stenosis severity assessment. Normally, however, according to a further aspect, data other than image data is not needed.

According to this step, the obtained patient specific anatomical data that has been obtained from imaging as discussed above may first be evaluated to determine if the image quality is acceptable. The image quality evaluation may be performed by a user via a visual assessment. Alternatively, the image quality of the image anatomical data may be evaluated through a semi-automatic assessment using readily available imaging viewer software. Still further, the image quality may be assessed automatically using a computer system. If the quality is not acceptable, the image anatomical data may be reacquired using any of the methods above.

According to an aspect, after the patient data, including anatomical imaging information, is obtained, a three-dimensional (3D) surface model of the patient vessel or lesion tree may be created, as generally indicated by reference number 12. According to another aspect, the 3D surface model created from the anatomical data may illustrate any lesions that exist in a patient's entire coronary tree. Alternatively, the 3D model may instead be of a smaller vessel tree that illustrates lesions of interest in the context of their upstream and/or downstream vessels. According to another aspect, the present disclosure is particularly suited to evaluate complex morphologies of lesions, such as lesions across bifurcations, distributed lesions, or the like. It will be appreciated that the present disclosure may also be utilized with simple morphologies of lesions that may exist in a single vessel branch, or regular or irregular shaped lesions.

According to an aspect, the 3D surface model of the vessel tree of cardiac lesions or the entire tree of the left anterior descending artery (LAD) or the right anterior descending artery (RCA) may be extracted from image data using cardiac workstation software or manual segmentation. It will be appreciated that a variety of other methods or techniques may be employed. According to an aspect, the 3D surface model may be in the form of either volume or surface data and can be converted to triangle based surface data. It will be appreciated that the 3D surface model can exist in a variety of other forms. According to another aspect, a centerline extraction algorithm may be applied if centerline data is not available. According to one aspect, the method may be performed automatically by a computer system, or semi-automatically by a user. Readily available software can be employed as will be understood by one of ordinary skill in the art.

Figure 4A:
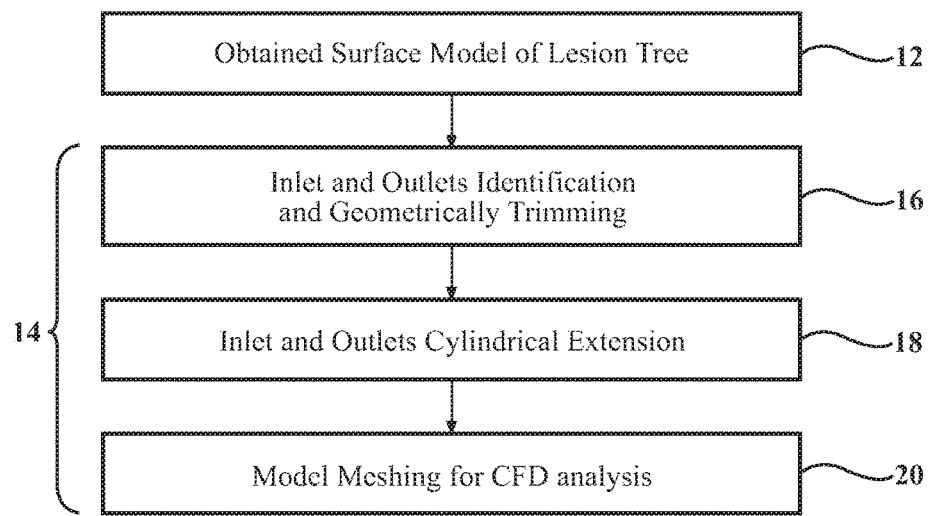
FIG. 4A illustrates a block diagram of pre-processing steps for a generated lesion tree model in accordance with an aspect of the disclosure.

According to an aspect and with reference to FIG. 3, once the 3D surface model has been created or generated, as generally indicted by reference number 12, the model may be subjected to preprocessing for further analysis, as generally indicated by reference number 14. According to an aspect and with reference to FIGS. 4A and 4B, the preprocessing may include the step of first identifying an inlet position and one or more outlet positions, as generally indicated by reference number 16. The inlet position and outlets position may be identified either by a manually seed picking method in 3D viewer using mouse clicks, or semi-automatically by utilizing centerline endpoints information. According to an aspect, only a single inlet is employed. As such, according to a further aspect, the LAD and RCA tree should be evaluated separately for stenosis severity.

According to an aspect, the step of preprocessing the model 14 can include the step of trimming the inlet branch and each of the outlets branches, as also generally indicated by reference number 16 as the entire vessel tree is not required to assess stenosis severity, as disclosed herein. It will be appreciated that the 3D model of the lesion tree may contain normal vessels leading to and from the site of any lesions, the analysis of which is not required. As such, according to an aspect, any normal vessel(s) or portion(s) of a normal vessel upstream or downstream of any lesions can be partly trimmed by removing them from the model. According to an aspect, the position of truncation of the vessel can be located some distance removed from the lesion site or position of any vessel branch. According to another aspect, if the inlet is very close to or at the lesion site, the truncation of the inlet can be minimal. Trimming the 3D model can provide benefits in that the size of the computational model may be reduced which will save time when performing the CFD calculation for testing flow simulation, as discussed herein. It will be appreciated that the degree of truncation may vary.

According to another aspect, the step of trimming the inlet and the outlets 16 can also include making the plane of the trimmed inlet and outlets perpendicular to an expected direction of blood flow. According to a further aspect, the flow direction can be the direction of the centerline for the extended outlets and inlet. According to a still further aspect, if the inlet position is close to a vessel branch and the centerline direction does not appear to be the proper direction of flow, manual adjusting of the trimming plane may be required such that it is perpendicular to proper flow direction.

According to another aspect, the pre-processing step can also include extending the inlet and the outlets into a circle shape, as generally indicated by reference number 18. This step can provide for ideal boundary conditions at the inlet and the outlets. According to an aspect, ideal boundary conditions can include a uniform pressure at all outlets. According to a further aspect, the length that each of the inlet and the outlets are extended may vary. According to another aspect, the inlet and outlets may be extended according to a predefined ratio between the length of the inlet/outlet extension and the diameter of inlet/outlet. An exemplary predefined ratio may be 16. However, a variety of other suitable ratios may be utilized. According to another aspect, the extended length section of the inlet and the outlets can contain two sections. The first section may be a smooth transition from the inlet/outlet boundary shape to a circle shape as reflected in the extended length section. The second section may be a short cylindrical pipe section that extends from the transition section (first section) to the inlet/outlet. According to another aspect, the cylindrical section length and transition section length may be controlled by various parameters or ratios. For example, the ratio of the lengths between the transition and cylindrical section may be selected as 1:3 with the pipe section being greater than the transition section. A variety of other suitable ratios may also be utilized.

According to a still further aspect, the pre-processing step can include a step of model meshing to prepare it for CFD analysis, as generally indicated by reference number 20. As will be understood, standard CFD needs a model in solid elements (tetrahedral elements for the disclosed CFD computation) instead of the surface model (triangle surface). The conversion from the surface model to solid elements is known as meshing. Either a free meshing tool, such as negen, gmesh, or a commercially accessible tool may be utilized.

Figure 4B:
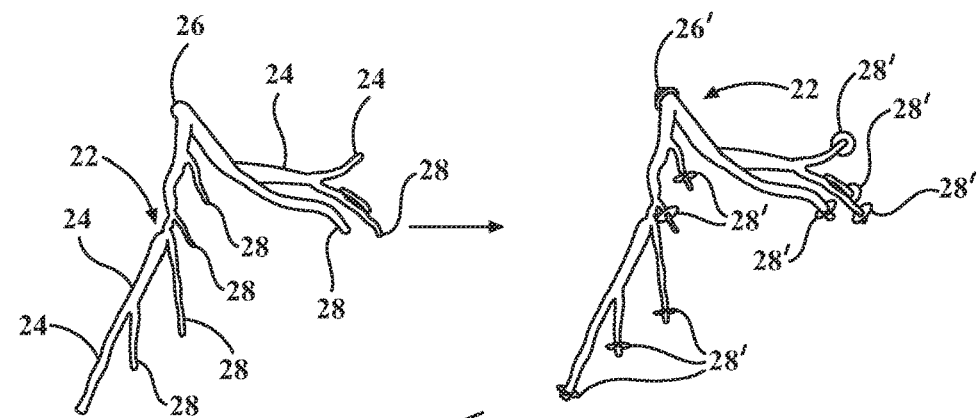
FIG. 4B schematically illustrates pre-processing steps on a generated lesion tree model in accordance with an aspect of the disclosure.
Figure 4B:
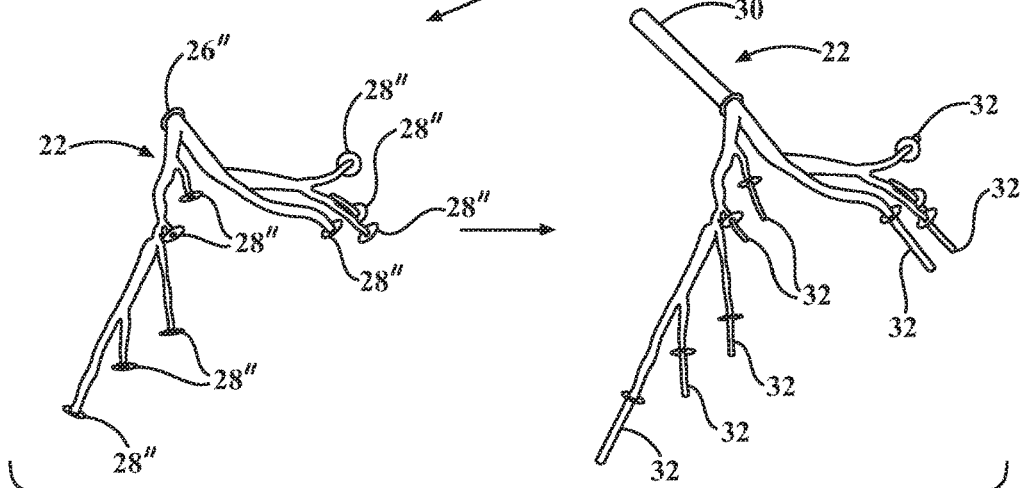

With reference to FIG. 4B, the steps of the exemplary pre-processing technique are graphically illustrated in the four images. Specifically, the upper left hand image depicts a 3D surface model of a lesion tree 22 as generated form the patient image data. The lesion tree model 22 can include a plurality of different branches 24. According to an aspect, the lesion tree 22 can include a single inlet 26 and a plurality of outlets 28. With reference to the upper right hand image, the step of identifying the inlet and the outlets is schematically shown by reference number 26' and 28'. According to a further aspect and with reference to the lower left hand image, the step of trimming the inlet 26' and each of the outlets 28' to remove unnecessary vessel portions along with the step of orienting the direction of the inlet and the outlets with the expected blood flow are schematically illustrated by reference numbers 26" and 28". According to a still further aspect, the lower right image illustrates the step of creating an inlet cylindrical extension 30 and outlet cylindrical extensions 32.

Figure 5:
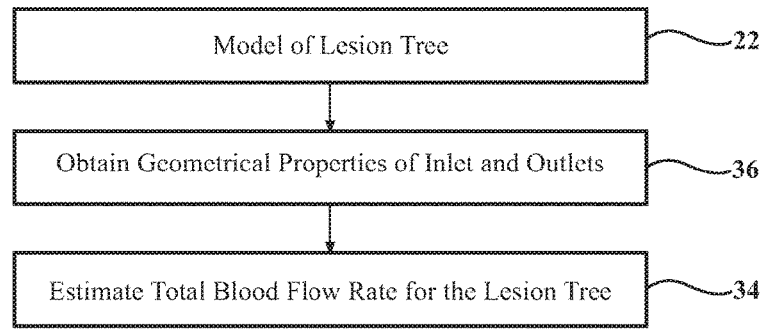
FIG. 5 illustrates a block diagram of a technique for total flow rate estimation of a testing flow for a pre-processed lesion tree model in accordance with an aspect of the disclosure.

According to an aspect, after the step of pre-processing the 3D model 14, the total flow rate that will be used for testing flow purposes may be estimated, as generally indicated by reference number 34. According to an aspect and with reference to FIG. 5, the total flow rate may be estimated from the lesion tree model 22 only. According to another aspect, a flow rate velocity that consists of a typical average velocity may be selected. An exemplary typical average velocity may be 20 cm/s. However, a variety of other estimated flow rates may be employed. According to an aspect, the estimated total flow rate may then be arrived at based on the product of the sum of the outlet areas and the selected average velocity.

According to another aspect, the geometric properties of the inlet 26 and the outlets 28 may be obtained, as generally indicated by reference number 36. According to an aspect, these geometric properties may be obtained during the preprocessing steps, as identified by reference number 16. According to a further aspect, these geometric properties can include diameter/area of the inlet/outlet and lengths of the extension. Thereafter, the total simulated blood flow rate for the lesion tree 22 may be estimated, as generally indicated by reference number 38. It will be appreciated that this process differs from FFRct's technology and other CFD applications which may require patient specific physiological blood flow rate and resulting complex blood flow demand estimation. According to an aspect, the disclosed method 10 may be more accommodating to flow rate differences across various patients. Alternatively, instead of utilizing a typical average velocity, the selected velocity may be adjusted based on basic patient information, such as patient weight. Accordingly, the disclosed method may employ a testing flow instead of physiological flow.

According to an aspect, the next step of the method may involve performing CFD simulation on the lesion model 22, as generally indicated by reference number 40. According to another aspect, with the estimated total flow rate of a testing flow, as generally indicated by reference number 34 and the generated 3D lesion model 22, general CFD methods can be performed for the purpose of obtaining flow properties and pressure gradient distribution of each of the outlets 28. Contrast this with FFRct which requires estimating the absolute pressure information in order to calculate the simulated FFR as well as modeling a complexed downstream resistance or other flow reaction for the CFD calculation.

According to an aspect, there may be a variety of different types of testing flows that may be employed which differ in boundary conditions. According to a further aspect, given the total flow rate for the testing flow as discussed below, in order to ease the CFD computation to solve the coupled variables of pressure and velocity and assign the boundary conditions at the outlets, a fixed variable either of pressure or velocity at the outlets can be selected, which will yield two types of testing flow conditions. According to an aspect, through the utilization of a testing flow, CFD results in relative pressure and flow rates, which can then be related with the severity of the blood flow obstruction.

Two defined types of exemplary testing flows that differ in boundary conditions are discussed herein in connection with FIG. 6. The first example testing flow type (I), as generally indicated by reference number 44, can involve utilizing a uniform pressure at each of the outlets 28. The second example testing flow type (II), as generally indicated by reference number 46, can involve utilizing fixed flow distributes at each of the outlets 28. According to an aspect, to perform a CFD calculation in accordance with the method 10 by utilizing the estimated total flow rate to determine the relative pressure, which makes the boundary conditions much simpler. Put another way, with one fixed variable at all the outlets, it makes the boundary condition much easier as it removes the interaction between the computational model and any complex downstream model, the need for which can be eliminated.

According to an aspect, the CFD simulation may be done with off the shelf software, such as OpenFoam (www.openfoam.com), Palabos (www.palabos.ort), conventional CFD software or custom developed software. Each simulation may yield a value for the force required to push the blood flow through the lesion given flow momentum where the force is the pressure drop between the inlet and the outlet. According to an aspect, the CFD simulation may also utilize fluid blood flow characteristics, such as blood density and viscosity. Typical blood density and viscosity values may be used. Upon completion of the CFD simulations, the pressure at the inlet is obtained and the dropped pressure between the inlet and outlet may be calculated.

Figure 6A:
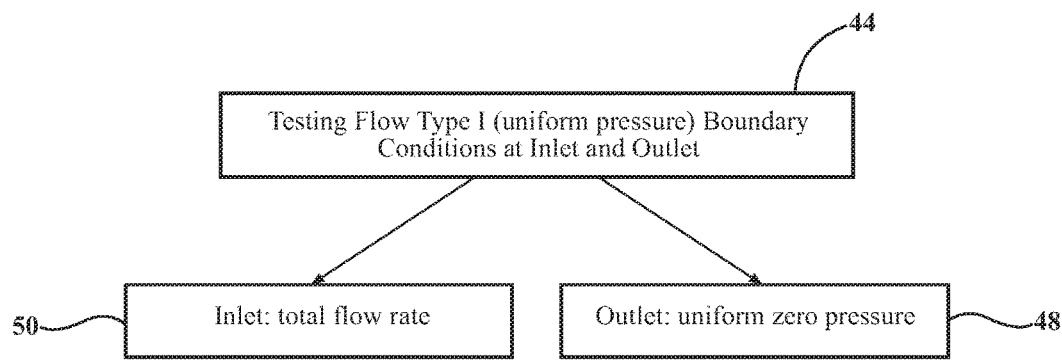
FIG. 6A schematically illustrates boundary conditions for a first exemplary testing flow type in accordance with an aspect of the disclosure.

With reference to FIG. 6A, according to an aspect, for the testing flow type (I) 44, a uniform pressure across all outlets may be employed, as generally indicated by reference number 48. According to another aspect, a zero pressure can be assigned to each of the outlets 28 for further calculation. According to an aspect, the CFD simulation will result in flow rate distributes across all the outlets. Additionally, the CFD simulation will determine a value for the inlet pressure. According to a further aspect, the interested inlet pressure and flow rates at outlets can be obtained from the simulated flow data after CFD simulation, as generally indicated by reference number 50.

Figure 6B:
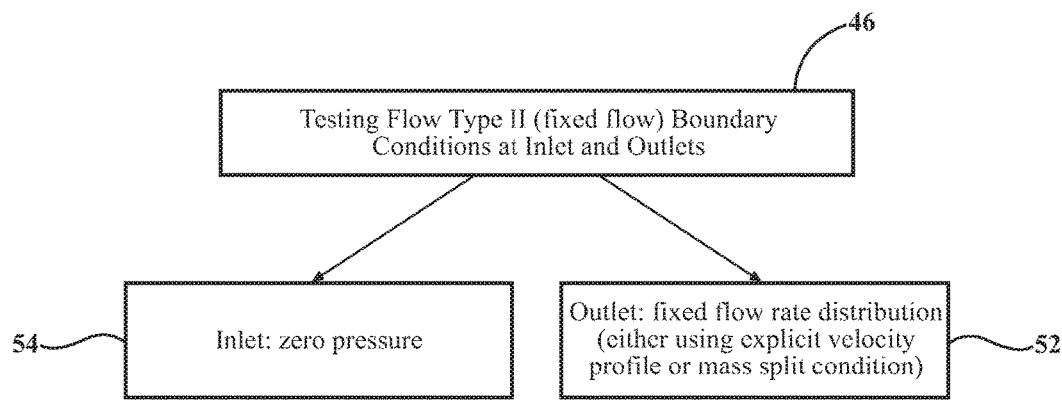
FIG. 6B schematically illustrates boundary conditions for a second exemplary testing flow type in accordance with an aspect of the disclosure.

According to an aspect and with reference to FIG. 6B, for the testing flow type (II) 46, fixed flow rates at each of the outlets 28 may be utilized. Given the total flow rates, the flow rate at each of the outlets 28 may be estimated, as generally represented by reference number 52. The flow rate at each of the outlets 28 may be selected based on the outlet radii following a generalization of Murray's law, which branches of normal vessels of a primary artery generally obey. For example, a normalized R^3 may be employed as the flow distribution weight for each outlet 28. According to another aspect, the boundary condition of the outlets 28 may be selected as an implicit flow rate distribute for some CFD packages or an explicit velocity profile calculated from laminar flow in a circle shape. Other suitable methods may also be employed. According to a still further aspect, the inlet pressure may be assigned a zero pressure, as generally indicated by reference number 54. Due to the flow rates for the outlets being estimated based on normal vessels, when a full block or extreme narrowing exists in one branch, the CFD calculation for this type may fail or be slow in convergence, indicating there is positive severity stenosis.

According to an aspect, the two testing flows may result in different flow rate distribution and apparent flow resistance for each outlet, and each can then be mapped to the appropriate two dimensional model. According to a further aspect, either of the two types of flow conditions can be independently used or both of them can be used to generate the final stenosis severity. According to a still further aspect, the final diagnosis of stenosis severity may be combined from the two testing flows by weighted sum or the maximum of them.

Figure 7:
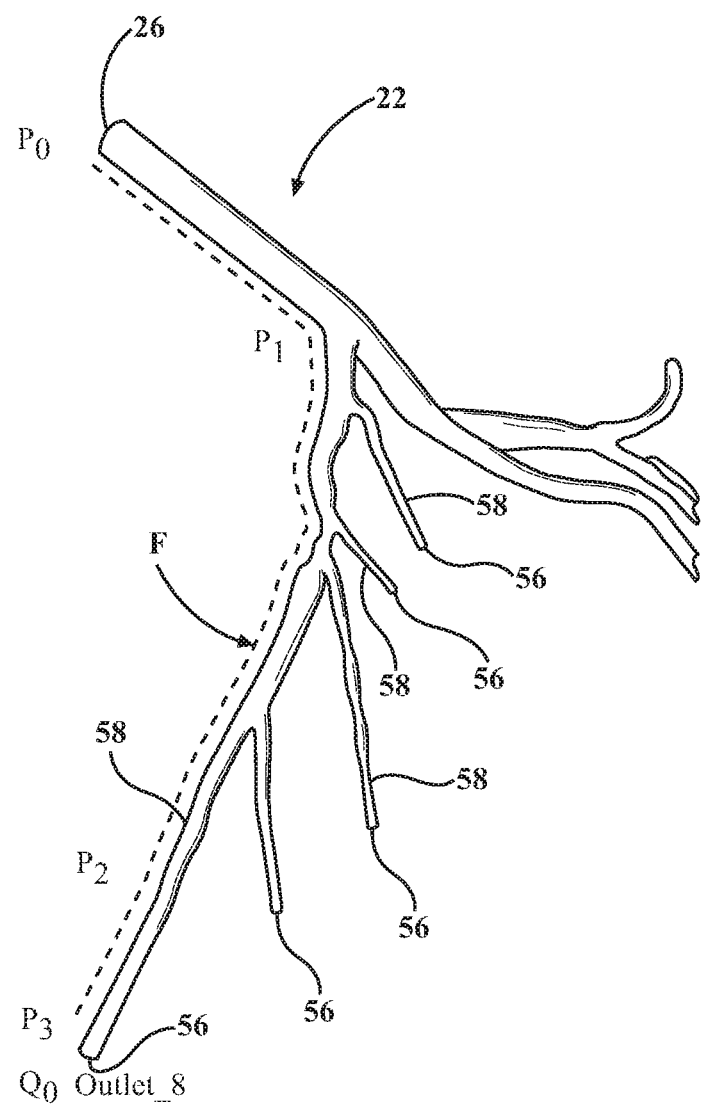
FIG. 7 schematically illustrates a method for calculating apparent flow resistance for a vessel outlet in accordance with an aspect of the disclosure.

With reference to FIG. 7, which schematically illustrates apparent flow resistance of an outlet and the apparent flow resistance. As shown, a lesion tree 22 can include an inlet 26 and a plurality of outlets 56. Between the inlet 26 and each of the outlets 56 are a plurality of different vessels 58. According to an aspect, the apparent flow resistance for any outlet may be calculated as a pressure gradient divided by flow rate (i.e, $R=(P_2-P_1)/Q_0$, where Q is the flow rate at the outlet and P is the pressure drop between the inlet and the outlet). According to an aspect, P0, P1, P2 and P3 are the pressures at different sample positions illustrated in FIG. 7. For each outlet, the flow rate may be obtained from the extended plane of the outlet 28. The pressure gradient may be the pressure drop between the inlet and outlets of the lesion tree 22, which should be sampled at the trimming position of the inlet and outlet. In other words, the pressure gradient should not include a pressure drop value on the extended section of the inlet and outlets. According to an aspect, after the CFD calculation of a testing flow on the lesion model, the flow rate and apparent flow resistance on each outlet are obtained. If both of the testing flow types are selected, a pair of such information will be obtained. In a multiple branched vessel system, the pressure between the inlet and outlet not only provides the forced and flow to the outlet, but also partially provides the force and flow to other branches, hence the apparent flow resistance has the effect from the flow to other branches, representing the flow characteristics of the branch under the flow environment for the lesion tree.

Figure 8:
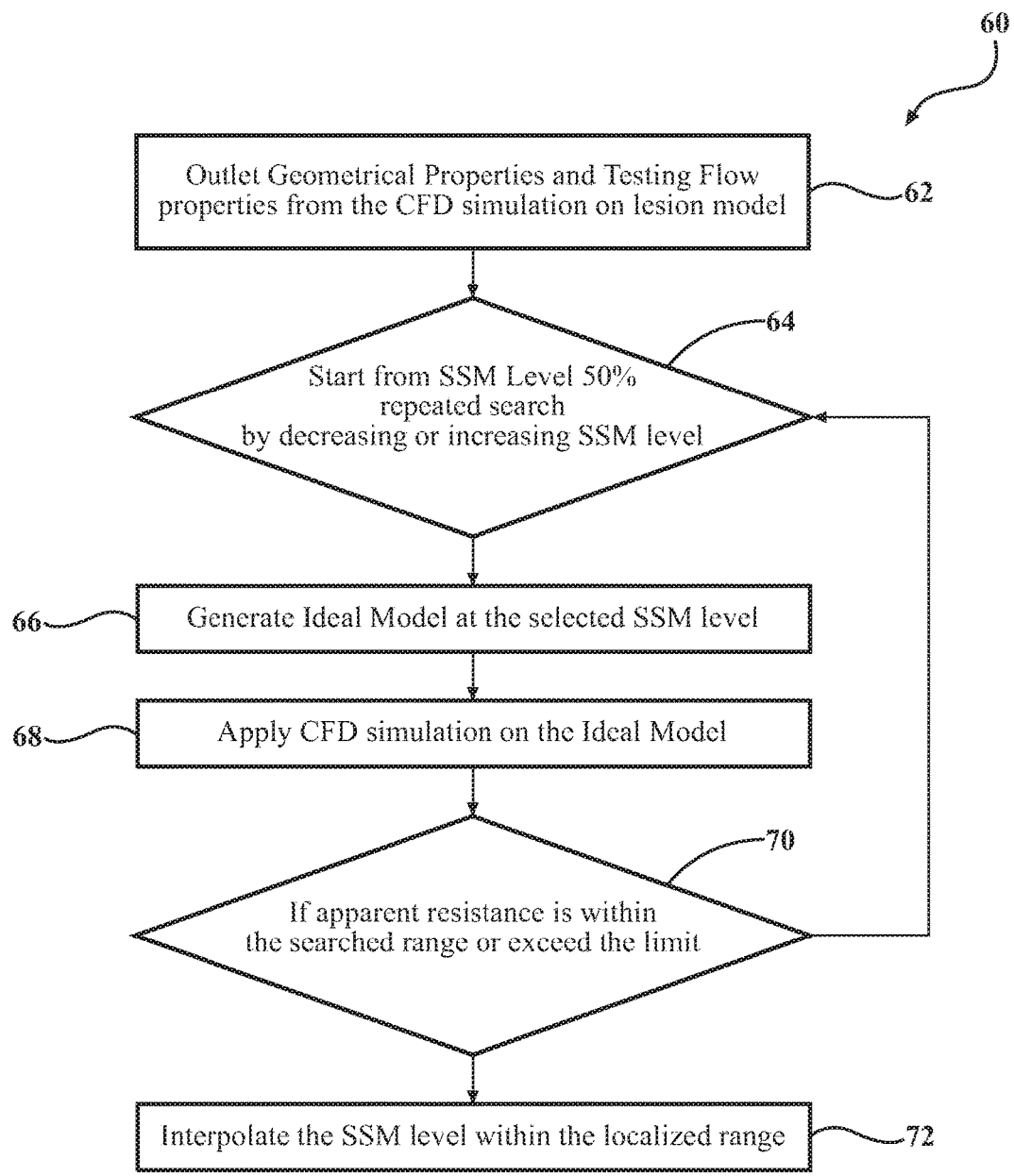
FIG. 8 illustrates a block diagram of exemplary stenosis severity search steps for determining a stenosis severity for a lesion tree model in accordance with an aspect of the disclosure.

FIG. 8 illustrates a step of searching for stenosis severity mapping. According to an aspect, given the obtained flow rate and resistance of each of the outlets 28, a search for a stenosis severity level may be applied to each outlet, as generally indicated by reference number 60. According to aspect, to determine a stenosis level at which to begin a comparison to the 3D model is selected as generally indicated by reference number 64. According to an aspect, a stenosis level of 50% may be selected and then the level can be increased or decreased from that level. Thereafter, an ideal model at the 50% stenosis level can be generated, as generally indicated by reference number 66. The ideal model can be generated based on the various control parameters as discussed herein in connection with FIGS. 9A and 9B. Also, a 3D or 2D for the axial symmetric model can be generated.

According to an aspect, a CFD simulation may be applied to the ideal stenosis model created, as generally indicted by reference number 68. According to an aspect, the same flow condition may be employed to obtain an apparent resistance between the end points (both the inlet and the outlet). The apparent flow resistance may then be analyzed to determine whether it is within the searched range or if it exceeds the limit, as generally indicated by reference number 70. According to an aspect, each outlet in the lesion tree will have one apparent resistance for one flow condition type. If the apparent resistance is within the searched range, the level of stenosis may be interpolated, as generally indicated by reference number 72. According to an aspect, if the apparent resistance is outside the searched ranges, the method 10 proceeds back up to step 64. As appropriate, the level of stenosis severity may be increased or decreased depending upon the obtained apparent resistance. According to an aspect, a new ideal model may then be generated at step 66 based on the new level of stenosis selected. According to another aspect, the steno sis severity search is done independently for each outlet. According to this aspect, a CFD simulation may be applied to this new ideal model, as generally indicated by reference number 68. Thereafter, the apparent resistance which results from the CFD simulation may be compared to the searched range to see if it exceeds the limit, as generally indicated by reference number 70. For example, if the apparent flow resistance is less than the apparent flow resistance of 30% or greater than 75%, the search can be stopped.

Figure 9A:
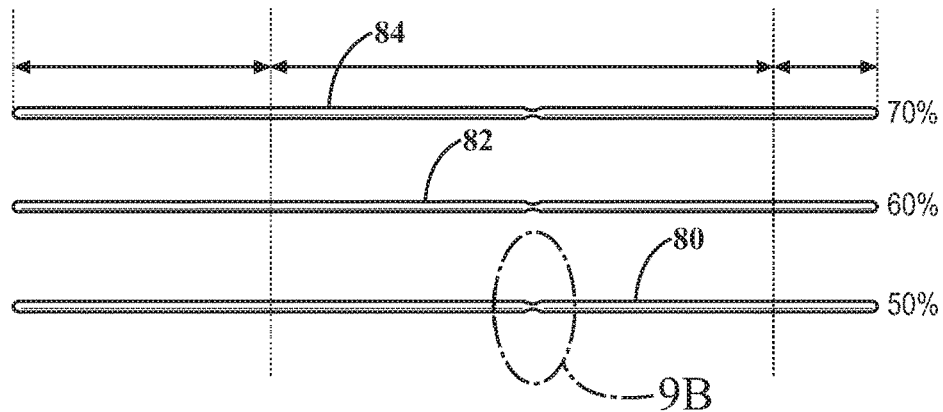
FIGS. 9A and 9B are schematic illustrations of exemplary ideal modes with various control parameters for an extended inlet and outlet in accordance with an aspect of the disclosure.

According to a further aspect and with reference to FIG. 9A, an exemplary ideal model 80 having a stenosis level 50% is schematically illustrated. According to an aspect, the ideal model 80 generally corresponds to the dashed vessel designated F in FIG. 7. It will be appreciated that this can apply to any other portion of the vessel tree model 22. According to an aspect, the search starts with the 50% stenosis model 80 and is compared to the vessel tree model 22. By way of example, if the apparent flow resistance for an outlet is R, and the apparent flow resistance of the 50% stenosis ideal model is R50, if R50 is smaller than R, the search can then continue with the 60% stenosis model 82 as generally indicated by reference number 64. According to an aspect, if the apparent resistance is not within the searched range, as generally indicated by reference number 70, the search can then continue with the 70% stenosis model 84. According to another aspect, the search can continue until the searched range is within 5% as generally indicated by reference number 72.

Figure 9B:
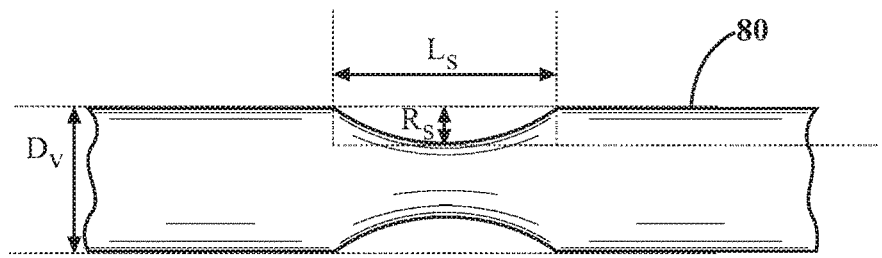

FIG. 9B is an enlarged view of the portion in the circle of GIF 9A and schematically illustrates a model of a level of stenosis severity and the control parameters used to generate same. According to an aspect, following parameters can be employed: (i) lesion path length which is the length of the centerline from the inlet to the outlet, (ii) the length of the inlet extension and the length of the outlet extension, (iii) the diameter of the outlet (Dv) (in the ideal model, the diameter is the same between the inlet/outlet), and (iv) the length Ls for the lesion model length which is 6 times of the Rs (stenosis reduction length).

Figure 10:
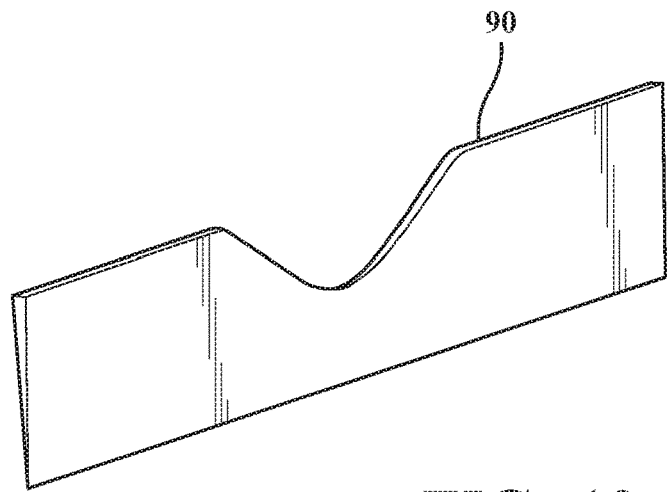
FIG. 10 is a schematic illustration of a stenosis model using a single layer of cells of a two dimensional (2D) wedged shape model for use with a finite volume (FVM) based accelerated computational fluid dynamic ("CFD") calculation in accordance with an aspect of the disclosure.

According to an aspect, FIG. 10 schematic illustrates a stenosis model 90 using a single layer of cells of a two dimensional (2D) wedged shape model for use with a finite volume (FVM) based accelerated computational fluid dynamic. Because of the nature of the axial symmetric shape of the ideal vessel/pipe with the embedded stenosis model, accelerated CFD computations may be available for both the standard FVM and FEM based CFD computations.

According to a further aspect, when using two types of testing flow conditions (i.e., type (I) and type (II), each testing will obtain a matched stenosis severity level. The final stenosis severity level will be a weighted sum of these levels. For example, let S0 and S1 be the stenosis severity levels from the two types of testing flow conditions, the final stenosis severity level can be expressed as S=(S0+S1)/2+ w*Abs(S0−S1), where the shift weight maybe 0.25.

Figure 11:
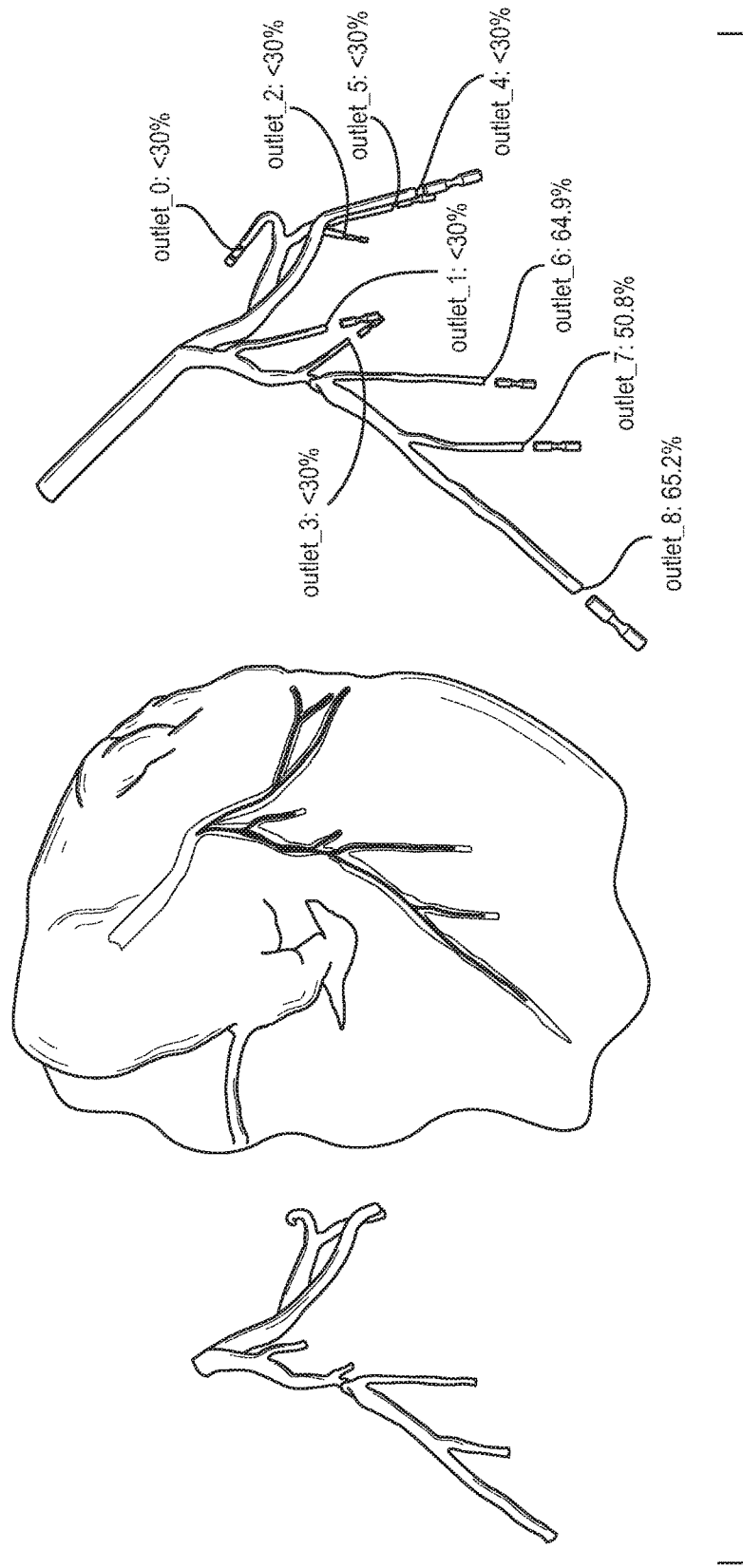
FIG. 11 schematically illustrates an exemplary visualization for stenosis severity mapping ("SSM") results on each outlet in a three dimensional ("3D") environment in accordance with an aspect of the disclosure.

FIG. 11 generally illustrates an exemplary visualization of stenosis severity mapping on each outlet in a three dimensional environment. The left hand image generally illustrates a lesion tree model 22 after preprocessing including trimming the inlets and outlets 16. The middle image in FIG. 11 schematically illustrates a volume rendering of the lesion tree model 22 including centerlines $C_L$ of each vessel. The right hand image of FIG. 11 illustrates a segment of the three dimensional ideal pip with embedded stenosis model at the associated severity level as attached to each outlet of the vessel. According to an aspect, the visualization allows users to quickly review the stenosis shape and the blood flow obstruction effect at each outlet.

Note that not all of the activities described above in the general description or the examples are required, that a portion of a specific activity may not be required, and that one or more further activities may be performed in addition to those described. Still further, the orders in which activities are listed are not necessarily the order in which they are performed.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Many other embodiments may be apparent to those of skill in the art upon reviewing the disclosure. Other embodiments may be used and derived from the disclosure, such that a structural substitution, logical substitution, or another change may be made without departing from the scope of the disclosure. Accordingly, the disclosure is to be regarded as illustrative rather than restrictive.

Certain features are, for clarity, described herein in the context of separate embodiments, may also be provided in combination in a single embodiment. Conversely, various features that are, for brevity, described in the context of a single embodiment, may also be provided separately or in any sub combination. Further, reference to values stated in ranges includes each and every value within that range.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The above-disclosed subject matter is to be considered illustrative, and not restrictive, and the appended claims are intended to cover any and all such modifications, enhancements, and other embodiments that fall within the scope of the present invention. Thus, to the maximum extent allowed by law, the scope of the present invention is to be determined by the broadest permissible interpretation of the following claims and their equivalents, and shall not be restricted or limited by the foregoing detailed description.

Although only a few exemplary embodiments have been described in detail above, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

What is claimed is:

1. A method of assessing stenosis severity for a patient, comprising:
   utilizing a processor associated with a computer system and task specific software to generate a three dimensional model of a lesion specific vessel tree of the patient;
   preprocessing the three dimensional model, including identifying a position for an inlet and positions for a plurality of outlets;
   estimating a total flow rate for the vessel tree model;
   providing perfusion conditions for a steady testing flow;
   utilizing the processor and the task specific software to perform computational fluid dynamic simulation on the vessel tree using the estimated total flow rate and provided perfusion conditions;
   determining apparent flow resistance for each of the outlets of the three dimensional model;
   utilizing the processor and the task specific software to generate at least one ideal stenosis model with a selected stenosis level;
   performing computational fluid dynamic simulation on the at least one ideal stenosis model to yield an ideal model apparent flow resistance; and
   determining a level of stenosis severity on each of the outlets of the patient vessel tree branch on a comparison of the three dimensional model to the at least one stenosis model; and
   wherein the step of determining a level of stenosis severity on each of the outlets of the patient vessel tree branch includes comparing the apparent flow resistance for each of the outlets with the ideal model apparent flow resistance of the at least one ideal stenosis model.

2. The method of claim 1, wherein the step of preprocessing further comprises:
   geometrically trimming the inlet and plurality of outlets to remove unnecessary portions of the vessel; and
   trimming the inlet and outlets such that they each reside in a plane perpendicular to an expected direction of flow.

3. The method of claim 1, wherein the step of preprocessing further includes:
   extending the inlet and the outlets into a circle shape to ensure ideal boundary conditions at the inlet and the outlets.

4. The method of claim 1, wherein the step of estimating the total flow rate for the vessel tree model includes selecting a typical average flow velocity for use with the computational fluid dynamic simulation.

5. The method of 1, wherein the step of performing computational fluid dynamic simulation includes selecting a type of testing flow for the purpose of this simulation.

6. The method of claim 5, wherein the testing flow type includes assigning a zero pressure to all outlets and the inlet is assigned either a total flow rate condition or an explicit velocity profile.

7. The method of claim 5, wherein the testing flow type includes assigning a fixed flow rate to each of the outlets, which fixed flow rate is an estimated value based on a radius of the outlets.

8. The method of claim 1, wherein the selected stenosis level of the least one ideal stenosis model is approximately 50%.

9. The method of claim 8, wherein the apparent flow resistance of the outlets of the three dimensional model is compared to the at least one ideal model flow resistance to determine if any difference therebetween is within or exceed a predetermined range.

10. The method of claim 9, wherein if the difference between the apparent flow resistances exceeds the predetermined range, a second ideal stenosis model is generated at a second selected stenosis level.

11. The method of claim 10, wherein a computational fluid dynamic simulation is applied to the second ideal stenosis model; and
   the apparent flow resistance of the three dimensional model is compared to an apparent flow resistance of the second ideal stenosis model to determine if any difference in the apparent flow resistances exceeds the predetermined range.

12. A method of assessing stenosis severity for a patient, comprising:
   utilizing a processor associated with a computer system and task specific software to generate a three dimensional model of a lesion specific vessel tree of the patient, the three dimensional model including an inlet and at least two outlets;
   estimating a total flow rate for the vessel tree model;
   utilizing the processor and the task specific software to perform computational fluid dynamic simulation on the vessel tree, the processor being configured to perform the computational fluid dynamic simulation for each of the at least two outlets using the estimated total flow rates;
   determining apparent flow resistance for each of the at least two outlets as a result of the computational fluid dynamic simulation;
   utilizing the processor and task specific software to generate at least one ideal stenosis model having a known level of stenosis severity;
   performing computational fluid dynamic simulation of the at least one ideal stenosis model to yield an apparent flow resistance for the at least one ideal stenosis model; and
   comparing the apparent flow resistance of at least one outlet of the three dimensional model to the apparent flow resistance of the at least one ideal stenosis model to identify an apparent flow resistance for the ideal stenosis model and to determine a level of stenosis severity of the patient vessel tree.

13. The method of claim 12, further comprising:
   preprocessing the three dimensional model, including identifying a position for an inlet and positions for the at least two outlets.

14. The method of claim 13, wherein the step of preprocessing further comprises:
   geometrically trimming the inlet and the at least two outlets to remove unnecessary portions of a vessel therebetween; and
   trimming the inlet and the at least two outlets such that they each reside in a plane perpendicular to an expected direction of flow.

15. The method of claim 13, wherein the step of preprocessing further includes:
   extending the inlet and the outlets into a circle shape to ensure ideal boundary conditions at the inlet and the at least two outlet.

16. The method of claim 12, wherein the step of estimating the total flow rate for the vessel tree model includes selecting a typical average flow velocity for use with the computational fluid dynamic simulation.

17. The method of 12, wherein the step of performing computational fluid dynamic simulation includes selecting a type of testing flow for the purpose of this simulation.

18. The method of claim 17, wherein the testing flow type includes assigning a zero pressure to the at least two outlets and the inlet is assigned either a total flow rate condition or an explicit velocity profile.

19. The method of claim 17, wherein the testing flow type includes assigning a fixed flow rate to each of the at least two outlets, which fixed flow rate is an estimated value based on a radius of the outlets.

20. The method of claim 12, wherein the comparing step includes utilizing an initial stenosis level of the least one ideal stenosis model of approximately.

21. The method of claim 12, wherein the step of comparing further includes comparing the apparent flow resistance of the at least one outlet of the three dimensional model to the at least one ideal model flow resistance of increased or decreased severity level to determine if any difference therebetween is within or exceeds a predetermined range.

22. The method of claim 21, wherein if the difference between the apparent flow resistances exceeds the predetermined range, the apparent flow resistance of the at least one model is compared to a flow resistance of a second ideal stenosis model to determine if any difference therebetween is within or exceeds the predetermined range.

* * * * *